US008809279B2

(12) United States Patent
Dal Farra et al.

(10) Patent No.: US 8,809,279 B2
(45) Date of Patent: Aug. 19, 2014

(54) PEPTIDES THAT ARE MODULATORS OF THE PROTEIN TRF2 AND COMPOSITIONS CONTAINING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 14/114,965

(22) PCT Filed: Apr. 27, 2012

(86) PCT No.: PCT/FR2012/000166
§ 371 (c)(1),
(2), (4) Date: Oct. 31, 2013

(87) PCT Pub. No.: WO2012/153015
PCT Pub. Date: Nov. 15, 2012

(65) Prior Publication Data
US 2014/0066381 A1 Mar. 6, 2014

(30) Foreign Application Priority Data
May 2, 2011 (FR) .................................. 11 01348

(51) Int. Cl.
*A61K 38/09* (2006.01)
*A61K 38/10* (2006.01)
*A61K 8/64* (2006.01)
*C07K 7/06* (2006.01)
*C07K 7/08* (2006.01)
*A61Q 19/00* (2006.01)
*A61Q 19/08* (2006.01)
*A61K 38/08* (2006.01)
*C07K 14/47* (2006.01)

(52) U.S. Cl.
CPC . *C07K 7/06* (2013.01); *A61K 38/08* (2013.01); *C07K 14/47* (2013.01)
USPC ......... 514/21.8; 514/1.1; 514/18.6; 514/18.8; 514/20.7; 514/21.5; 514/21.6; 514/21.7; 530/327; 530/328; 530/329; 530/330

(58) Field of Classification Search
CPC ............ C07K 7/06; C07K 7/08; A61Q 19/00; A61Q 19/08; A61K 38/09; A61K 38/10; A61K 8/64
USPC .......... 530/327, 328, 329, 330; 514/1.1, 18.6, 514/18.8, 20.7, 21.5, 21.6, 21.7, 21.8
See application file for complete search history.

(56) References Cited

U.S. PATENT DOCUMENTS

| 2002/0076719 | A1 | 6/2002 | Lange et al. | |
| 2009/0119794 | A1* | 5/2009 | Van Wordragen et al. | ... 800/278 |
| 2009/0176205 | A1* | 7/2009 | Nishimura et al. | ............... 435/6 |

FOREIGN PATENT DOCUMENTS

| EP | 1721972 | 11/2006 |
| WO | 98/36066 | 8/1998 |
| WO | 99/15662 | 4/1999 |
| WO | 01/44266 | 6/2001 |
| WO | 2004/092395 | 10/2004 |

OTHER PUBLICATIONS

International Search Report, International Application No. PCT/FR2012/000166 (mailed Oct. 2, 2012, published Sep. 10, 2012).
Bilaud, T. et al., "The Telebox, A Myb-Related Telomeric DNA Binding Motif Found in Proteins From Yeast, Plants and Human," Nucleic Acids Research, Oxford University Press, Surrey, GB, vol. 24, No. 7, pp. 1294-1303 (Apr. 1, 1996).
Kullmann, et al., "Proteases as Catalysts for Enzymic Syntheses of Opioid Peptides," The Journal of Biological Chemistry, vol. 255, No. 17, pp. 8234-8238 (Sep. 10, 1980).

\* cited by examiner

*Primary Examiner* — Julie Ha
(74) *Attorney, Agent, or Firm* — Thompson Hine L.L.P.

(57) ABSTRACT

Peptide compounds of the following general formula (I):

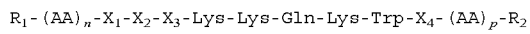

$R_1-(AA)_n-X_1-X_2-X_3-Lys-Lys-Gln-Lys-Trp-X_4-(AA)_p-R_2$ are disclosed herein. The peptide compounds can be used as Telomeric repeat-binding factor 2 (TRF2) protein-modulating compounds and have a preventive action on deoxyribonucleic acid (DNA) double-strand breaks. In addition, cosmetic compositions that include at least one peptide of general formula (I) in a physiologically acceptable medium are disclosed along with methods for preventing and/or treating cutaneous signs of aging and photoaging.

18 Claims, No Drawings

```
                       SEQUENCE LISTING

<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 1

Asn Thr Lys Lys Gln Lys Trp Thr Asn
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 2

Lys Lys Gln Lys Trp
1               5

<210> SEQ ID NO 3
<211> LENGTH: 11
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 3

Gly Gly Leu Lys Lys Gln Lys Trp Asn Leu Tyr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 4

Ala Met Lys Lys Gln Lys Trp
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 5

Ala Leu Ser Lys Lys Gln Lys Trp Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 6

Cys Lys Lys Gln Lys Trp Ser
1               5
```

PEPTIDES THAT ARE MODULATORS OF THE PROTEIN TRF2 AND COMPOSITIONS CONTAINING SAME

The present invention concerns the field of cosmetics. It relates to peptide compounds of the following general formula (I):

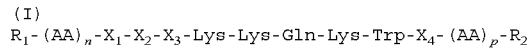

as TRF2 protein-modulating compounds, thus having a telomere protection action and a preventive action on DNA double-strand breaks. Said peptide compounds included in a cosmetic composition are intended to prevent and/or delay and/or treat cutaneous signs of aging.

Senescence is a biological process that affects all cells "normally" comprising a human being. Physically, this involves general aging of the human body, whether they are skin cells, hair cells, organ cells, etc.

It has been scientifically demonstrated that senescence is caused in particular by the shortening of telomeres (replicative senescence) or by acute or chronic exposure to physiological stress signals such as, for example, oxidative stresses. One of the means explored for limiting cellular senescence and therefore limiting manifestations of aging in human beings consists of acting on the shortening of telomeres and/or limiting the action of oxidative stresses on DNA.

Telomeres are formed by repetitions of the sequence TTAGGG and specific proteins. Telomeres are located at the ends of the chromosomes and ensure the stability of same. Among the proteins that are associated with telomeres are the TRF1 and TRF2 proteins (TRF for telomere-binding factor), which bind directly to the double-strand telomeric DNA, or the POT1 protein, which, itself, binds to the single-strand end 3'. In cell divisions, TTAGGG motifs are lost in transit during replication. This loss of telomeres is partially compensated for by a reverse transcriptase, telomerase, which synthesizes de novo telomeric repetitions on preexisting telomere ends, thereby ensuring an optimal length. The problem that arises is that the activity of this telomerase is extremely low in somatic cells, leading to a telomeric shortening in each chromosomal replication. One of the strategies currently used to limit skin aging as well as manifestations of same consists of increasing the telomerase activity of the skin cells. However, this leads to immortalization of said cells, which is undesirable because immortalized cells may be related to cancerous cells.

The applicant explored another approach to attempting to delay cellular senescence, by modulating the quantity of telomere-associated proteins, and more specifically the TRF2 protein. Thus, the applicant developed peptide compounds of the following general formula (I):

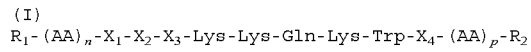

Said compounds are capable of preventing and/or delaying and/or treating the cutaneous signs of aging by modulating the quantity of telomere-associated proteins (TRFs). They are also useful for preventing the occurrence of DNA double-strand breaks in skin cells upon damage, owing to modulation of the quantity of TRF proteins present in the cell.

TRF protein-modulating compounds or telomere stabilizers have previously been proposed as described in patent applications US20020076719, WO9836066, or WO2004092395. However, none of the above-cited documents describes or discloses peptide compounds as disclosed in the present patent application, or the cosmetic use of such compounds as an agent fighting cutaneous signs of aging.

The present invention therefore relates firstly to a peptide compound of the following general formula (I):

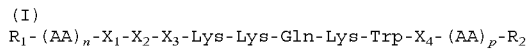

The present invention secondly relates to a cosmetic composition including, as an active principle, said peptide compound of formula (I).

In addition, the present invention relates thirdly to the cosmetic use of a composition including said peptide compound of formula (I) for preventing and/or delaying and/or treating the cutaneous signs of aging. In particular, said cosmetic composition will be useful (i) for modulating the quantity of telomere-associated proteins (TRFs) and/or delaying senescence in skin cells, (ii) for preventing the occurrence of DNA double-strand breaks in skin cells upon damage, (iii) for preventing and/or treating the cutaneous signs of photo-aging of the skin, and, finally (iv) for protecting the skin from external stresses.

Finally, the present invention relates fourthly to a method for cosmetic treatment of the skin or skin appendages to be treated by means of the composition including said peptide compound of formula (I), or a method for cosmetic treatment by means of the peptide according to the invention for limiting the degradation of the telomeres without modifying the quantity and/or the activity of the telomerase.

The peptide compounds according to the invention are characterized in that they:
- modulate the quantity of telomere-associated proteins (TRFs) and in particular the TRF2 protein;
- limit the increase and aggregation of the protein of the Vimentin cytoskeleton in cells having an aged cell phenotype;
- limit the appearance of damage in biopsies of skin subjected to methylglyoxal; and
- make it possible, in conclusion, to prevent and/or delay and/or treat the signs of senescence in the cells treated.

The present invention firstly relates to a peptide compound of general formula (I):

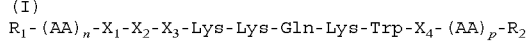

wherein:

$X_1$ represents an asparagine, a glycine, a threonine, an alanine or no amino acid, $X_2$ represents an isoleucine, a leucine, a methionine, a proline, or no amino acid, $X_3$ represents a threonine, an asparagine, a serine or no amino acid, $X_4$ represents a serine, a cysteine, a threonine, an asparagine, a glutamine or no amino acid, AA represents any amino acid, and n and p are integers between 0 and 2, $R_1$ represents the primary amine function of the N-terminal amino acid, —$NH_2$, wherein one of the two hydrogen atoms may or may not be substituted by an acetyl-type saturated or unsaturated $C_1$ to $C_{30}$ alkyl chain, or by an aromatic group of the benzoyl, tosyl or benzyloxycarbonyl type, $R_2$ represents the hydroxyl group of the carboxyl function of the C-terminal amino acid, —OH, wherein the hydrogen atom may or may not be substituted by a $C_1$ to $C_{30}$ alkyl chain, or an $NH_2$, NHY or NYY group, wherein Y represents a $C_1$ to $C_4$ alkyl chain, said sequence of general formula (I) consisting of 5 to 13 amino acid residues.

The term "peptide compound" or "peptide" refers to a chain of two or more amino acids bound to one another by peptide bonds or by modified peptide bonds.

"Peptide compound" or "peptide" means the natural or synthetic peptide of the invention as described above, or at least one of its fragments, whether it is obtained by proteolysis or synthetically, or any natural or synthetic peptide of which the sequence consists entirely or partially of the sequence of the peptide described above.

The amino acids constituting the peptide compound according to the invention can be in the levorotatory, i.e. L-, and/or the dextrorotatory, i.e. D-configuration. The peptide according to the invention can therefore be in the form L-, D- or DL-.

To improve resistance to degradation, it may be necessary to use a protected form of the peptide according to the invention. The form of protection must obviously be a biologically compatible form and must be compatible with use in the field of cosmetics. Preferably, to protect the primary amine function of the N-terminal amino acid, a substitution with an $R_1$ group of the acyl type having a saturated or unsaturated $C_1$ to $C_{30}$ alkyl chain, capable of being chosen from an acetyl group or an aromatic group, is used. Preferably, to protect the carboxyl function of the C-terminal amino acid, a substitution with an $R_2$ group of the $C_1$ to $C_{30}$ alkyl chain, or an $NH_2$, NHY or NYY group with Y representing a $C_1$ to $C_4$ alkyl chain, is used.

The peptide according to the invention can be protected at the N-terminal or C-terminal end or at both ends.

In a first embodiment of the invention, in the general formula (I), n and p are equal to zero and the sequence of general formula (I) consists of 5 to 9 amino acid residues. This therefore means that, in general formula (I):

$X_1$ represents an asparagine, a glycine, a threonine, an alanine or no amino acid, $X_2$ represents an isoleucine, a leucine, a methionine, a proline, or no amino acid, $X_3$ represents a threonine, an asparagine, a serine or no amino acid, $X_4$ represents a serine, a cysteine, a threonine, an asparagine, a glutamine or no amino acid, the integers n and p are equal to zero, $R_1$ represents the primary amine function of the N-terminal amino acid, —$NH_2$, wherein one of the two hydrogen atoms may or may not be substituted by an acetyl-type saturated or unsaturated $C_1$ to $C_{30}$ alkyl chain, or by an aromatic group of the benzoyl, tosyl or benzyloxycarbonyl type, $R_2$ represents the hydroxyl group of the carboxyl function of the C-terminal amino acid, —OH, wherein the hydrogen atom may or may not be substituted by a $C_1$ to $C_{30}$ alkyl chain, or an $NH_2$, NHY or NYY group, wherein Y represents a $C_1$ to $C_4$ alkyl chain, said sequence of general formula (I) consisting of 5 to 9 amino acid residues.

In a second preferred embodiment, the peptide compound corresponds to one of the following formulas:

```
                                           (SEQ ID NO: 1)
Asn-Thr-Lys-Lys-Gln-Lys-Trp-Thr-Asn-NH2;

(SEQ ID NO: 2)
Lys-Lys-Gln-Lys-Trp-NH2;

(SEQ ID NO: 3)
Gly-Gly-Leu-Lys-Lys-Gln-Lys-Trp-Asn-Leu-Tyr;

(SEQ ID NO: 4)
Ala-Met-Lys-Lys-Gln-Lys-Trp-NH2;

(SEQ ID NO: 5)
Ala-Leu-Ser-Lys-Lys-Gln-Lys-Trp-Gln;
and
                                           (SEQ ID NO: 6)
Cys-Lys-Lys-Gln-Lys-Trp-Ser-NH2,
```

The invention also relates to homologous forms of these sequences. The term "homologous", according to the invention, refers to any peptide sequence at least 50%, or preferably at least 80%, and even more preferably at least 90% identical to said peptide sequence, chosen from sequences SEQ ID NO: 1 to SEQ ID NO: 6. The phrase "peptide sequence at least X % identical" means a percentage of identity between the amino acid residues of the two sequences to be compared, obtained after optimal alignment of the two sequences. The optimal alignment is obtained by means of local homology algorithms such as those used by the BLAST P computer software program available at the NCBI site.

The term "homologous" can also refer to a peptide that differs from the sequence of a peptide of sequence SEQ ID NO: 1 to SEQ ID NO: 6 by the substitution of chemically equivalent amino acids, i.e. by the substitution of one residue by another one having the same characteristics. Thus, the classic substitutions are made between Ala, Val, Leu and Ile; between Ser and Thr; between the acid residues Asp and Glu; between Asn and Gln; and between the basic residues Lys and Arg; or between the aromatic residues Phe and Tyr.

The peptide of general formula (I) according to the invention can be obtained either by classic chemical synthesis (in solid phase or in homogeneous liquid phase), or by enzymatic synthesis (Kullmann et al., J. Biol. Chem. 1980; 225: 8234) using constituent amino acids or derivatives of same.

The peptide according to the invention can be of natural or synthetic origin. Preferably, according to the invention, the peptide is obtained by chemical synthesis.

Finally, the active principle can be a single peptide, a mixture of peptides or peptide derivatives and/or consist of amino acid derivatives.

According to an advantageous embodiment of the invention, the peptide compound according to the invention is solubilized in one or more physiologically suitable solvents, classically used by a person skilled in the art, such as water, glycerol, ethanol, propanediol, butylene glycol, dipropylene glycol, ethoxylated or propoxylated diglycols, cyclic polyols or any mixture of these solvents.

According to yet another advantageous embodiment of the invention, the peptide compound according to the invention is solubilized in a cosmetic or pharmaceutical vector such as liposomes, or adsorbed on powdery organic polymers, mineral supports such as talcs and bentonites, and more generally solubilized in, or fixed on, any physiologically suitable vector.

The present invention relates secondly to a cosmetic composition including, as an active principle, said peptide compound of general formula (I).

Preferably, the compositions according to the invention are in a form suitable for topical application including a cosmetically acceptable medium. By "cosmetically acceptable", we mean media that are suitable for use in contact with human skin or skin appendages, without risk of toxicity, incompatibility, instability, allergic response or the like. The compositions intended to be applied to the skin can be in the form of a cream, an oil-in-water emulsion, or a water-in-oil or multiple emulsion, a solution, a suspension, a microemulsion, an aqueous or anhydrous gel, a serum or a vesicle dispersion, a patch, a spray, an ointment, a pomade, a lotion, a colloid, a milk, a lotion, a stick or a powder, all suitable for application on the skin, lips and/or skin appendages.

Preferably, said peptide compound is present in the composition at a concentration of between around 0.1 and 500 ppm, and preferably at a concentration of between 1 and 150 ppm.

Even more preferably, the composition according to the invention also contains at least one other active principle. It is possible to cite, in a non-limiting manner, the following classes of ingredients: plant peptide hydrolysates, other peptide compounds, sunscreens, anti-free radical agents or anti-wrinkle agents. It is also possible to cite vitamin C and derivatives thereof, B vitamins, DHEA (dehydroepiandrosterone), phytosterols, salicylic acid and derivatives thereof, retinoids, flavonoids, sugar amines, azoles, metal salts, or polymers.

The composition can also include healing, anti-aging, anti-wrinkle, soothing, hydrating, and anti-inflammatory agents, agents modulating differentiation, skin pigmentation or depigmentation, and so on.

In a more specific embodiment, the composition according to the invention will include, in addition to the peptide compound of formula (I):
- one (or more) cytochrome c-activating compound, and/or;
- one (or more) aquaporin-activating compound and/or;
- one (or more) sirtuin-activating compound and/or;
- one (or more) compound that increases cell adhesion and/or;
- one (or more) compound that increases the production of matrix proteins of the collagen or laminin type, etc.;
- one (or more) hsp protein-modulating compound;
- one (or more) compound that increases cell energy;
- one (or more) compound improving the skin barrier function;
- one (or more) compound improving cell synchronization, such as, for example, agents modulating Clock, Perl or Bmal proteins;
- one (or more) mitochondria-protecting compound.

Said compounds above can be natural, such as plant peptide or non-peptide hydrolysates, or of synthetic origin, such as peptide compounds.

In addition, additives such as solvents, diluents, dyes, sunscreens, self-tanning agents, pigments, fillers, preservatives, odor absorbents, thickening agents, emulsifiers, moistening agents, emollients, fragrances, antioxidants, film-forming agents, chelating agents, sequestering agents and conditioners can be added to the composition.

In every case, a person skilled in the art will make sure that these adjuvants as well as the proportions thereof are chosen so as not to adversely affect the desired advantageous properties of the composition according to the invention. These adjuvants can be, for example, between 0.01 and 20% of the total weight of the composition. When the composition of the invention is an emulsion, the fatty phase can be 5 to 80% by weight, and preferably 5 to 50% by weight with respect to the total weight of the composition. The emulsifiers and co-emulsifiers used in the composition will be chosen among those classically used in the field considered. For example, they may be used in a proportion ranging from 0.3 to 30% by weight with respect to the total weight of the composition.

The invention relates thirdly to the cosmetic use of a composition including said peptide compound in a cosmetically acceptable medium for preventing and/or delaying and/or treating cutaneous signs of aging. "Cutaneous signs of aging" include, but are not limited to, any manifestations visible on the skin caused by aging. This means, in particular, wrinkles, deep and rough lines, small wrinkles, cracks, loosening of cutaneous and subcutaneous tissue, loss of cutaneous elasticity and atonia, loss of firmness and tone, and dermal atrophy. In addition, "cutaneous signs of aging" refers to enlarged pores, imperfections, discoloration, age spots, keratoses, collagen loss, and other changes in the dermis and epidermis, but also all modifications of the external appearance of the skin and skin appendages due to aging, such as, for example, surface roughness of the stratum corneum, and also any internal modification of the skin that does not systematically involve a modified exterior aspect, such as, for example, the thinning of the dermis.

In a first embodiment of the invention, said cosmetic composition makes it possible to modulate the quantity of telomere-associated proteins and/or delay senescence in skin cells. The phrase "modulate the quantity of telomere-associated proteins (TRFs)" refers to increasing or decreasing the quantity of TRF proteins present in the cells, or increasing/decreasing the protein synthesis of same (by direct or indirect modulation of gene expression), or by other biological processes such as stabilization/destabilization of the RNA messenger transcripts. Preferably, the TRF proteins are represented by the TRF2 and/or POT1 proteins.

In a second preferred embodiment of the invention, the cosmetic composition is used to prevent the occurrence of DNA double-strand breaks in skin cells upon damage. Indeed, in damage inflicted upon skin cells, in particular damage due to UV radiation or oxidative stress, the DNA of said cells may be subject to damage manifested by double-strand breaks. The peptide compounds according to the invention demonstrated their DNA-protective action with respect to this type of damage.

Another use of the peptide according to the invention consists of preventing and/or treating cutaneous signs of photoaging of the skin. "Photoaging" refers to premature aging of the skin caused by prolonged and cumulative exposure to the sun.

The peptide according to the invention can also be used to protect the skin from external stresses. "External stresses" refers to stresses that can be produced by the environment. For example, it is possible to cite stresses such as pollution, UV radiation, stresses causing oxidative stress, or irritating products such as surfactants, preservatives or fragrances, mechanical stresses, such as abrasions, shaving or hair removal. However, preferably, the external stresses consist primarily of UV radiation, and in particular UVB radiation, and the stresses cause oxidative stress.

Finally, the invention relates lastly to a cosmetic treatment method characterized by the application, in the morning and evening, on the skin, of a composition including an effective quantity of the peptide compound as defined above, for preventing and/or treating cutaneous signs of aging. Another embodiment of the present invention involves implementing a method for cosmetic treatment of the skin by means of a composition according to the invention, so as to limit telomere degradation without modifying the quantity and/or activity of telomerase. In effect, the peptide according to the invention makes it possible to stabilize and/or limit telomere degradation without affecting the activity and/or the quantity of telomerase, which is important because there will thus be no risk of cell immortalization.

The following examples describe and demonstrate the efficacy of peptide compounds as described in the invention, but must not be interpreted as limiting the present invention.

EXAMPLE 1

Study of the Effect of the Peptide SEQ ID NO: 2 on Fibroblasts Aged by Replicative Senescence Human fibroblasts are placed in culture in a specific medium and kept in culture for a long treatment (for more than 17 passages), by means of a daily application of the peptide SEQ ID NO: 2 at a concentration of 1% or of 3%. A vimentin immunofluorescence detection experiment is performed on the cells in culture passages 6 and 17. The cells are then washed with PBS, fixed with 3.7% formaldehyde for 10 minutes, permeabilized by means of 0.2% Triton X-100 for 10 minutes (Fisher Chemical) and incubated with 1% BSA (Euromedex) for 15 minutes. An anti-vimentin antibody (Tebu Santa Cruz) is then added and incubated at a dilution of 1/200 for 2 h at room temperature. After washing with PBS, a Donkey anti-mouse IgG antibody, conjugated with a marker ALEXA FLUOR® 488, is added at a dilution of 1/1000 and incubated for one hour at room temperature. Finally, the sections are mounted with Fluoromount G (Electron Microscopy Science) and examined under a microscope (Nikon Eclipse 80i, enlargement 40×).

Results/Conclusions:

It is noted that the aged fibroblasts treated with the peptide SEQ ID NO: 2 express less vimentin than the aged fibroblasts not treated. The increase and aggregation of vimentin is associated with modifications in the cytoskeleton that accompany the aging phenomenon. It can therefore be concluded that the treatment with the peptide compound SEQ ID NO: 2 according to the invention made it possible to limit the increase and aggregation of vimentin due to aging of the fibroblasts.

EXAMPLE 2

Study of the Effect of the Peptide SEQ ID NO: 4 on a Model of Biopsies Rendered Senescent In Vitro Using Methylglyoxal Human skin biopsies are rendered artificially senescent in vitro, by means of a treatment with methylglyoxal (MGO). For this, des punch de 6-mm human skin punch biopsies are incubated at the air-liquid interface in a specific culture medium. They are then treated with 5 mM or 10 mM of MGO (Sigma) deposited at the surface of the biopsies and in the culture medium. The biopsies are then treated with:
  condition 1: 20 µL of PBS 1×, or
  condition 2: 20 µL of peptide SEQ ID NO: 4 at 1%, or
  condition 3: 20 µL of peptide SEQ ID NO: 4 at 3%.

The biopsies are fixed and embedded in paraffin, and are then cut into 4-µm sections using a microtome. Hematoxyline/eosine (H&E) immunolabeling is performed on the sections previously cut and their morphology and structure are studied by microscopic observation (under a microscope Nikon Eclipse E600, objective 40×).

Results/Conclusions:

In the control 1 condition, i.e. without the addition of peptide, it is noted that the MGO caused significant damage to the skin biopsies, more precisely to the structure of same. The damage caused is dose-dependent, as more damage is observed with the quantity of 10 µM of MGO.

When the biopsies are treated with the peptide compound SEQ ID NO: 4, it is noted that the damage inflicted on the structures of said biopsies is much less significant than under the control conditions. It is noted that the protective effect of the peptide is dose-dependent, as even less damage is observed with the 3% dose than with the 1% dose.

It can thus be concluded that the peptide SEQ ID NO: 4 had a protective effect on the cellular structures when they are subjected to stresses leading to significant damage and premature senescence.

EXAMPLE 3

Study of the Expression of the TRF2 Protein by siRNA in Human Fibroblasts Treated with the Peptide SEQ ID NO: 2

To quantify the efficacy of a peptide compound according to the invention, on the overexpression of TRF2 in a human fibroblast population, the gene coding for TRF2 was "turned off" by using the siRNA technique.

Protocol:

Fibroblast cells are placed in culture in a 6-well plate until 60% confluence. The culture medium is renewed by adding the peptide SEQ ID NO: 2 at 1% under the conditions described below. Then, 100 µL of a mixture previously produced containing, in the end, 10 nM of TRF2 siRNA and the transfection agent are gently added, one drop at a time, and one well at a time. The cell culture plate is incubated at 37° C. and 5% in $CO_2$ for 72 h. The culture medium is renewed every 2 days. Four conditions were established:
  condition 1: control without siRNA and without active agent
  condition 2: cells transfected with the siRNA, without active agent
  condition 3: cells not transfected but treated with the active agent
  condition 4: cells transfected with the siRNA and treated with the active agent The quantification of the TRF2 expression is observed by the classic immunotransfer technique (Western Blot) performed with an anti-TRF2 antibody and according to a classic protocol. To analyze the compensation provided by the peptide in the fibroblasts having been transfected with the siRNA, the comparison will be made with respect to untreated fibroblasts of which the gene was not turned off by siRNA.

Results/Conclusions:

Between conditions 1 and 3, it is noted that the addition of the peptide led to a 17% increase in the expression of the TRF2 protein with respect to the control. Between conditions 1 and 2, the effect of the siRNA on the expression of the TRF2 protein is clearly noted: in effect, it decreases by 26%. However, the addition of the active agent to the cells transfected with the siRNA makes it possible to restore the TRF2 expression, and the reduction due to the presence of siRNA is no more than 18% with respect to the control condition.

In conclusion, the active agent according to the invention made it possible to compensate for the reduction in the expression of the TRF2 protein (reduction induced by the specific siRNA) in the fibroblasts treated.

EXAMPLE 4

Composition of an Anti-Aging Face Cream

| Trade names | INCI names | % by weight |
|---|---|---|
| Phase A | | |
| MONTANOV 68 ® | Cetearyl Alcohol (and) Cetearyl Glucoside | 6.00 |
| Squalane | Squalane | 3.00 |
| ISP BONJOUR ® Refined shea butter | *Butyrospermum Parkii* (Shea Butter) | 2.00 |
| WAGLINOL 250 ® | Cetearyl Ethylhexanoate | 3.00 |
| Amerchol L-101 ® | Mineral Oil (and) Lanolin Alcohol | 2.00 |
| SI-TEC DM 350 ® | Dimethicone | 1.50 |
| BHT | BHT | 0.01 |
| Coenzyme Q10 | Ubiquinone | 0.10 |
| Phase B | | |
| Avocado oil | *Persea Gratissima* (Avocado) Oil | 1.25 |
| OPTIPHEN ® | Phenoxyethanol (and) Caprylyl Clycol | 1 |
| Phase C | | |
| Demineralized water | Aqua (Water) | qsf |
| Butylene Glycol | Butylene Glycol | 2.00 |
| GLUCAM E10 ® | Methyl Gluceth-10 | 1.00 |
| Allantoin | Allantoin | 0.15 |
| CARBOPOL ULTREZ 10 ® | Carbomer | 0.20 |
| Phase D | | |
| TEA | Triethanolamine | 0.18 |
| Phase E | | |
| Peptide SEQ ID NO: 5 | | 3 mg/kg |
| GP4G ® | Water (and) Artemia Extract | 1.50 |
| COLLAXYL ® | Water (and) Butylene Glycol (and) Hexapeptide-9 | 3.00 |
| Phase F | | |
| Fragrance | Fragrance | qsf |
| Dye | | qsf |

Prepare and melt phase A at 65-70° C. Heat phase C at 65-70° C. Phase B is added to phase A just before emulsifying A in C. At around 45° C., the carbomer is neutralized by adding phase D. At around 30° C., phase E is then added under light stirring and the cooling is continued until 25° C. Phase F is then added if desired.

Applicants incorporate by reference the material contained in the accompanying computer readable Sequence Listing entitled "US11-153 SEQUENCE LISTING", which was created on Oct. 30, 2013, and is 1,589 bytes in size.

The invention claimed is:

1. A peptide compound of the following general formula (I):

$$R_1\text{-}(AA)_n\text{-}X_1\text{-}X_2\text{-}X_3\text{-}Lys\text{-}Lys\text{-}Gln\text{-}Lys\text{-}Trp\text{-}X_4\text{-}(AA)_p\text{-}R_2$$

wherein, $X_1$ is an asparagine, a glycine, a threonine, an alanine or absent, $X_2$ is an isoleucine, a leucine, a methionine, a proline, or absent, $X_3$ is a threonine, an asparagine, a serine or absent, $X_4$ is a serine, a cysteine, a threonine, an asparagine, a glutamine or absent, AA is any amino acid, and n and p are integers between 0 and 2, $R_1$ is the primary amine function of the N-terminal amino acid, —$NH_2$, wherein one of the two hydrogen atoms may or may not be substituted by an acetyl-type saturated or unsaturated $C_1$ to $C_{30}$ alkyl chain, or by an aromatic group of the benzoyl, tosyl, or benzyloxycarbonyl type, $R_2$ is the hydroxyl group of the carboxyl function of the C-terminal amino acid, —OH, wherein the hydrogen atom is substituted by a $C_1$ to $C_{30}$ alkyl chain, or an $NH_2$, NHY or NYY group, wherein Y is a $C_1$ to $C_4$ alkyl chain;
said peptide compound of general formula (I) consisting of 5 to 13 amino acid residues.

2. The peptide compound according to claim 1, wherein n and p are equal to zero and in that said sequence of general formula (I) consists of 5 to 9 amino acid residues.

3. The peptide compound according to claim 1, wherein the peptide compound is selected from the group consisting of:
(SEQ ID NO: 1) Asn-Thr-Lys-Lys-Gln-Lys-Trp-Thr-Asn-NH$_2$;
(SEQ ID NO: 2) Lys-Lys-Gln-Lys-Trp-NH$_2$;
(SEQ ID NO: 3) Gly-Gly-Leu-Lys-Lys-Gln-Lys-Trp-Asn-Leu-Tyr-NH$_2$;
(SEQ ID NO: 4) Ala-Met-Lys-Lys-Gln-Lys-Trp-NH$_2$;
(SEQ ID NO: 5) Ala-Leu-Ser-Lys-Lys-Gln-Lys-Trp-Gln-NH$_2$; and
(SEQ ID NO: 6) Cys-Lys-Lys-Gln-Lys-Trp-Ser-NH$_2$.

4. The peptide compound according to claim 1, wherein the peptide compound is solubilized in one or more physiologically suitable solvents chosen from water, glycerol, ethanol, propanediol, butylene glycol, dipropylene glycol, ethoxylated or propoxylated diglycols, cyclic polyols or any mixture of these solvents.

5. A cosmetic composition comprising: a peptide compound, as an active principle, in a cosmetically acceptable medium, the peptide compound having the following general formula (I):

$$R_1-(AA)_n-X_1-X_2-X_3-Lys-Lys-Gln-Lys-Trp-X_4-(AA)_p-R_2$$

wherein,
$X_1$ is an asparagine, a glycine, a threonine, an alanine or absent,
$X_2$ is an isoleucine, a leucine, a methionine, a proline, or absent,
$X_3$ is a threonine, an asparagine, a serine or absent,
$X_4$ is a serine, a cysteine, a threonine, an asparagine, a glutamine or absent,
AA is any amino acid, and n and p are integers between 0 and 2,
$R_1$ is the primary amine function of the N-terminal amino acid, —NH$_2$, wherein one of the two hydrogen atoms may or may not be substituted by an acetyl-type saturated or unsaturated $C_1$ to $C_{30}$ alkyl chain, or by an aromatic group of the benzoyl, tosyl, or benzyloxycarbonyl type,
$R_2$ is the hydroxyl group of the carboxyl function of the C-terminal amino acid, —OH, wherein the hydrogen atom is substituted by a $C_1$ to $C_{30}$ alkyl chain, or an NH$_2$, NHY or NYY group, wherein Y is a $C_1$ to $C_4$ alkyl chain;
said peptide compound of general formula (I) consisting of 5 to 13 amino acid residues.

6. The composition according to claim 5, wherein the composition is in a form suitable for topical application, selected from the group consisting of a cream, an oil-in-water emulsion, or a water-in-oil or multiple emulsion, a solution, a suspension, a microemulsion, an aqueous or anhydrous gel, a serum or a vesicle dispersion, a patch, a spray, an ointment, a pomade, a lotion, a colloid, a milk, a stick, and a powder.

7. The composition according to claim 5, wherein said peptide compound is present in the composition at a concentration of between about 0.1 and 500 parts per million (ppm).

8. The composition according to claim 7, wherein said peptide compound is present in the composition at a concentration of between about 1 and 150 parts per million (ppm).

9. The composition according to claim 6, wherein the composition further comprises at least one other active principle selected from the group consisting of plant peptide hydrolysates, other peptide compounds, sunscreens, anti-free radical agents or anti-wrinkle agents.

10. A method for cosmetic treatment, the method comprising:
applying to skin a composition comprising an effective quantity of a peptide compound having the following general formula (I):

$$R_1-(AA)_n-X_1-X_2-X_3-Lys-Lys-Gln-Lys-Trp-X_4-(AA)_p-R_2$$

wherein,
$X_1$ is an asparagine, a glycine, a threonine, an alanine or absent,
$X_2$ is an isoleucine, a leucine, a methionine, a proline, or absent,
$X_3$ is a threonine, an asparagine, a serine or absent,
$X_4$ is a serine, a cysteine, a threonine, an asparagine, a glutamine or absent,
AA is any amino acid, and n and p are integers between 0 and 2,
$R_1$ is the primary amine function of the N-terminal amino acid, —NH$_2$, wherein one of the two hydrogen atoms may or may not be substituted by an acetyl-type saturated or unsaturated $C_1$ to $C_{30}$ alkyl chain, or by an aromatic group of the benzoyl, tosyl, or benzyloxycarbonyl type,
$R_2$ is the hydroxyl group of the carboxyl function of the C-terminal amino acid, —OH, wherein the hydrogen atom is substituted by a $C_1$ to $C_{30}$ alkyl chain, or an NH$_2$, NHY or NYY group, wherein Y is a $C_1$ to $C_4$ alkyl chain;
said peptide compound of general formula (I) consisting of 5 to 13 amino acid residues.

11. The method of claim 10, wherein the peptide compound is an active agent that limits the degradation of telomeres without modifying the quantity and/or the activity of telomerase.

12. The method of claim 10, wherein applying to the skin comprises applying in the morning and applying in the evening.

13. The method of claim 10, wherein the cosmetic treatment comprises applying daily the peptide compound as an active agent, wherein the effective quantity of the peptide compound in the composition is between about 0.1 and 500 parts per million and is effective to delay cutaneous signs of aging, treat cutaneous signs of aging, delay cutaneous signs of photoaging, and/or treat cutaneous signs of photoaging.

14. The method of claim 10, wherein the effective quantity of peptide compound in the composition is between about 0.1 and 500 parts per million and is an amount effective to modulate the quantity of telomere-associated proteins (Telomeric repeat-binding factor (TRFs)), and/or delay senescence in skin cells.

15. The method of claim 14, wherein the telomere-associated proteins comprise one or more Telomeric repeat-binding factor 2 (TRF2) and Protection of Telomere 1 (POT1).

16. The method of claim 10, wherein the cosmetic treatment comprises applying the peptide compound after skin cells are damaged by ultraviolet (UV) radiation or oxidative stress.

17. The method of claim 13, wherein the cutaneous signs of aging comprise one or more of wrinkles, deep and rough lines, small wrinkles, cracks, loosening of cutaneous and subcutaneous tissue, loss of cutaneous elasticity and atonia, loss of firmness and tone, and dermal atrophy.

18. The method of claim 10, wherein the cosmetic treatment comprises applying the peptide compound to the skin before exposure to one or more of ultraviolet (UV) radiation and oxidative stress.

* * * * *

UNITED STATES PATENT AND TRADEMARK OFFICE
CERTIFICATE OF CORRECTION

| | | |
|---|---|---|
| PATENT NO. | : 8,809,279 B2 | Page 1 of 1 |
| APPLICATION NO. | : 14/114965 | |
| DATED | : August 19, 2014 | |
| INVENTOR(S) | : Claude Dal Farra, Nouha Domloge and Jean-Marie Botto | |

It is certified that error appears in the above-identified patent and that said Letters Patent is hereby corrected as shown below:

In the Specification

Column 10, Lines 28-29, it reads:
"entitled 'US11-153 SEQUENCE LISTING' which was created on Oct. 3.0, 2013, and is 1,589 bytes in size."

It should read:
-- entitled "11-153SEQ_ST25", which was created on April 23, 2014, and is 1,716 bytes in size. --

Signed and Sealed this
Sixteenth Day of December, 2014

Michelle K. Lee
*Deputy Director of the United States Patent and Trademark Office*